United States Patent [19]

Royster, Jr.

[11] 4,035,482

[45] July 12, 1977

[54] RODENTICIDE CONTAINING QUININE SALTS

[76] Inventor: Percy L. Royster, Jr., 731 Georgia Ave., Brooklyn, N.Y. 11207

[21] Appl. No.: 145,920

[22] Filed: May 21, 1971

[51] Int. Cl.² .......................................... A01N 13/00
[52] U.S. Cl. .................................. 424/134; 43/124; 424/17; 424/133; 424/259
[58] Field of Search ............. 424/133, 134, 259, 17

[56] References Cited

PUBLICATIONS

Stedman's Medical Dictionary, 20th ed., 1961, p. 1422.

Primary Examiner—Leonard Schenkman
Attorney, Agent, or Firm—Amster & Rothstein

[57] ABSTRACT

A rodenticide composition comprising an edible bait, an arsenic-based poison and a quinine salt provides improved kill rates and accelerated kill times. Repeated feedings of the composition without the poison produces an increased appetite in rats and therefore aids in the effectiveness of the poisonous composition.

5 Claims, No Drawings

RODENTICIDE CONTAINING QUININE SALTS

This invention relates generally to a rodenticide. More specifically, this invention relates to an improved poisonous compound and method suitable for the accelerated extermination of rats and mice.

It is well known in the art to employ arsenic compounds as a poison in the extermination of rodents. Such compounds have not been altogether satisfactory for several reasons. First, the action of the arsenic poison is relatively slow and thus the time required to kill a rodent may be in excess of 24 to 48 hours. As a result, rodents which have eaten the poison may be widely dispersed and collection and disposal may become significant problemns particularly in view of the potential health hazards stemming from decay. Second, and more importantly, unless sufficient quantitites of the poison are ingested by the rodent, the poison may only produce sickness rather than extermination thereby increasing, rather than reducing, the health hazard.

It is an object of the present invention to provide an improved composition and method for more rapidly killing rodents.

It is another object of the invention to provide an improved poison composition and method having a significantly higher lethal dosage coefficient than conventional arsenic-based poisons.

Yet another object of the invention is to provide an economical method of exterminating rodents in which the quantity of poison and other ingredients employed in the rodenticide are efficiently uitlized.

The above and other objects of the invention are achieved by a novel composition including a quinine salt and an arsenic-based poison. It has now been discovered that the use of quinine in a rodenticide greatly accelerates both the kill time and kill rate of rodents. While not wishing to be limited to any particular theory, it is presently believed that the quinine compounds serve to increase the circulation of the poison when ingested by rodents thereby causing a faster reaction to the poison. In addition, it appears that the presence of the quinine compounds increases the rodents' appetite for the bait thereby causing it to devour more than a normal amount of food and a greater amount of poison. Thus, the rodenticides prepared and used in accordance with the invention exhibit greatly accelerated kill times and kill rates.

The compositions of the invention comprise a mixture of conventional bait, an arsenic-based poison and a quinine salt such as quinine sulfate and preferably quinine hydrochloride. Both the poison and the food bait are conventional. Thus, the preferred poison is a finely ground commercial white arsenic, also known as arsenic trioxide, or arsenious acid although other poison compounds which have heretofore been employed in rodenticides may also be used in the compositions of the invention either alone or in combination with the arsenic poison. The bait or carrier may be any edible food product or mixtures thereof which are palatable to rats. A wide range of such materials have heretofore been used in poison compositions and the present invention is not limited to the utilization of a particular carrier. Typical edible food products which may be employed in the composition are meat, fish and vegetable products; for example, ground salmon, sardines, sardine oil, corn, oats, molasses, peanut oil and the like.

The composition of the invention is prepared by thoroughly mixing approximately 1.0 to 20 wt.% of an arsenic-based poison, e.g. 2 ounces per pound of bait, with 1.0 to 10.0 wt.% of the quinine compound, e.g. 1 ounce per pound of bait, and 70 to 98 wt.% of a bait, e.g., an edible food carrier. It will be obvious to those persons skilled in the art that the relative amount of arsenic and the quinine composition are not critical and that somewhat lesser or greater amounts of each compound may be employed without departing from the scope of the invention.

When the above described composition is dispersed in any conventional fashion, it will produce improved kill times and kill rates as compared to conventional rodenticides. However, in one preferred method of utilizing the composition of the invention in order to maximize its benefits, the bait traps will be pre-baited, at regular baiting intervals commonly employed in the art on at least one or more occasions with a composition including the quinine compound but excluding the poison. In another preferred embodiment the bait containing the quinine compound but not containing any poison will be employed on at least two successive regular baiting intervals, preferably 3 to 7 baiting intervals and the amount of quinine employed in the bait composition for each successive baiting interval will be greater than that employed in the composition used in the preceding interval. Thus, for example, the method of the invention will involve dispersing a first bait composition comprising a food carrier containing a small amount of the quinine compound, for example, 1 to 2 wt.%; subsequently dispersing a second bait composition at the next normal baiting interval in which the bait composition is identical to the first composition except that it contains an increased amount of the quinine compound, for example, 2-4 wt.%; and subsequently dispersing the final bait composition which includes the poison.

It has been found that by eating a bait containing the quinine compounds of the invention, the rodents develop a greater appetite so that when the poison containng composition is finally employed, abnormally large amounts of bait and therefore of poison will be eaten thereby further enhancing the effectiveness of the rodenticide composition. It will be obvious to those persons skilled in the art that any number of feedings of quinine-containing bait may be employed without departing from the scope of the invention.

The invention will be further understood by reference to the following illustrative examples.

EXAMPLE 1

A rodenticide bait was prepared by mixing the following ingredients:

| INGREDIENT: | AMOUNT: |
| --- | --- |
| Crushed Corn | 25 lbs. |
| Fish Oil | 1.5 gallons |
| Molasses | 0.5 gallons |
| Quinine Hydrochloride | 2.5 lbs. |
| White Arsenic | 3.2 lbs. |

The above composition (Composition A) was used in a testing program as a rat poison. It was compared with a rat poison composition (Composition B) which was substantially identical to that described above with the exception that the quinine hydrochloride was omitted.

A series of tests were conducted using approximately 50 trapped live field rats for each test. In each test 2.5 to 5.0 lbs. of either Composition A, or Composition B was placed in a cage containing the field rats. After each feeding the rats were observed to determine both the kill rate and the time required to kill rats.

As a result of several tests it was determined that Composition A, containing the quinine compound, killed an average of 87% (38 out of the 50) of the rats in an average time period of 4 to 7 hours. Composition B which did not include the quinine compound killed an average of approximately 60% (30 out of 50) of the rats and required an average time period of 24 hours to accomplish this result.

EXAMPLE 2.

Compositions similar to those described in Example 1 but excluding the arsenic poison were employed in a series of tests to determine the affinity of the rats for the bait. In each test approximately 25 to 50 trapped live field rats were fed a weighed amount of the bait composition. After each feeding the remaining bait was removed and weighed to determine the amount of bait consumed. By weighing the group of rats before each experiment it was possible to determine the amount of bait consumed per pound of rat.

As a result of several experiments it was determined that commencing with the second feeding, the consumption of the composition containing the quinine compound, was 14 to 27 wt.% greater than the composition which did not contain the quinine compound.

When the poison containing composition (Composition A) was used subsequent to the administration of non-poisonous bait in a series of trials, the lethal dose rate averaged 87% and kill times ranged from 1 to 38 minutes with the rats showing pronounced distress in 2 to 6 minutes.

Having thus described the general nature, as well as the specific embodiments of the invention, the true scope will now be pointed out in the appended claims.

What is claimed is:

1. A poison composition comprising an edible bait, 1 to 20 wt.% of a arsenic poison, and 1 to 10 wt.% of a quinine salt.
2. The composition of claim 1 wherein said quinine salt is selected from the group consisting of quinine sulfate and quinine hydrochloride.
3. The composition of claim 1 wherein said quinine salt is quinine hydrochloride.
4. A rodenticide composition comprising an edible bait, 1 to 20 wt.% white arsenic and 1 to 10 wt.% of a quinine salt.
5. The composition of claim 4 wherein said quinine salt is quinine hydrochloride.

* * * * *